United States Patent [19]
Bom et al.

[11] Patent Number: 5,176,141
[45] Date of Patent: Jan. 5, 1993

[54] DISPOSABLE INTRA-LUMINAL ULTRASONIC INSTRUMENT

[75] Inventors: Nicolaas Bom, Berkenwoude; Charles T. Lancee, Waarder, both of Netherlands

[73] Assignee: Du-Med B.V., Overschieseweg, Netherlands

[21] Appl. No.: 591,652

[22] Filed: Oct. 2, 1990

[30] Foreign Application Priority Data

Oct. 16, 1989 [NL] Netherlands .................. 8902559

[51] Int. Cl.⁵ .............................................. A61B 8/12
[52] U.S. Cl. .............................................. 128/662.06
[58] Field of Search ............... 128/660.03, 662.06, 128/4, 772

[56] References Cited

U.S. PATENT DOCUMENTS

| | | | |
|---|---|---|---|
| 4,375,818 | 3/1983 | Suwaki et al. | 128/662.06 |
| 4,487,605 | 12/1989 | Angelsen et al. | 128/660.03 |
| 4,494,549 | 1/1985 | Namba et al. | 128/662.06 |
| 4,908,808 | 3/1990 | Knapen et al. | 368/157 |
| 5,000,185 | 3/1991 | Yock | 128/662.06 |
| 5,029,588 | 7/1991 | Yock et al. | 128/662.06 |

OTHER PUBLICATIONS

Schmidt, J. E., "Attorney's Dictionary of Medicine", Matthew Bender Publ., New York, N.Y. ©1980 p. L-77.

Bom, N. et al. "Early and Recent Intra-Luminal Devices", International Journal of Cardiac Imaging 4: 79-88 1989.

*Primary Examiner*—Francis Jaworski
*Attorney, Agent, or Firm*—Thomas R. Vigil; James P. Hanrath

[57] ABSTRACT

The disposable intra-luminal ultrasonic instrument for the examination and/or treatment of blood vessels and similar lumina has a small transverse cross-section. The instrument includes a catheter comprising a body and a tip having a distal end and a distal portion adapted to be introduced into a lumen and a proximal portion. The catheter has a diameter no greater than 3 millimeters, a rotatable member in the tip, a small motor in the tip and coupled to the rotatable member for rotating the rotatable member at a selected rpm, and means for generating and supplying sound waves to, the rotatable member at a frequency no greater than 60 megahertz.

11 Claims, 2 Drawing Sheets

DISPOSABLE INTRA-LUMINAL ULTRASONIC INSTRUMENT

BACKGROUND OF THE INVENTION

1. Field of the Invention

The present invention relates to a disposable intraluminal ultrasonic instrument which includes a catheter that has a sound wave transducer therein and a rotatable acoustic mirror for directing the sound waves outwardly into tissue and for receiving echo sounds and directing the echo sounds to the transducer for transmission to a visual display which displays an ultrasound picture of the tissue whereby one can determine the makeup or constitution of the tissue, e.g., hard or soft. More particularly, the present invention relates to such an instrument wherein the catheter tip is not greater than 3 millimeters in diameter and has mounted therein a very small electric motor for rotating the acoustic mirror while the transducer provides sound waves to the acoustic mirror at a frequency no greater than 60 megahertz.

2. Description of the related art including information disclosed under 37 CFR Sections 1.97–1.99.

Heretofore it has been proposed in Dutch Patent Application No. 87.00632 to provide a catheter having a catheter tip with a rotatable acoustic mirror therein or a rotatable tip having an acoustic mirror therein. A flexible shaft extends from the rotatable acoustic mirror to the proximal end of the catheter where it is driven by a suitable motor situated outside the catheter. A transducer is mounted in the catheter tip opposite the rotatable acoustic mirror. Rotation of the acoustic mirror within the tip or the tip portion having the mirror thereon causes high frequency ultrasonic vibrations or sound waves emitted by the transducer to be emitted in different directions in a rotating path and the echoes of the sound waves are received by the acoustic mirror and thence by the transducer for transmission to a visual display whereby a picture can be created of the space around the catheter tip which may contain tissue or a stenotic buildup in a vessel.

A problem with the instrument having the catheter described above is that the flexible drive shaft is fairly long, i.e., at least as long as the catheter itself. With this arrangement, it is difficult to supply a torsion free rotational force through the flexible drive shaft and to drive such a long flexible drive shaft for extended periods of time without malfunctioning.

As will be described in greater detail below, the present invention provides an intra-luminal ultrasonic instrument which does not have the problem of a long drive shaft by providing a small motor in the catheter tip for driving a short drive shaft coupled to an acoustic mirror in the catheter tip.

It has been suggested in Dutch Patent Application No. 87.00632 to provide a turbine driven by fluid at or near the catheter tip with the turbine having a short drive shaft coupled to the rotatable acoustic mirror.

Heretofore it has been proposed in European Patent Application Publication No. 0 139 574 to provide an endocavity probe having a motor mounted in the distal end of one embodiment of the probe. The motor rotates a mirror which reflects signals emitted by a transducer.

This probe is utilized in examining organs and the like of a body. The probe is somewhat bulky in shape and size, is intended for insertion in body cavities, is not suitable for insertion inside veins and/or arteries and does not teach a motor having a diameter no greater than 3 millimeters in a catheter tip.

In the Sakai German Offenlegungsschrift DE 32 19 118 A1 there is disclosed an endoscope having a metal housing in which is mounted a rotatable mirror and a motor for rotating the mirror. Also fiber optics are provided for viewing capabilities. This patent publication does not disclose or suggest a catheter tip no greater than 3 millimeters in diameter having a motor mounted therein for rotating an acoustic mirror positioned adjacent to a transducer in the catheter tip.

The Eggleton et al. U.S. Pat. No. 4,546,771 discloses an acoustic microscope which has a transducer capable of producing and receiving high frequency acoustical beams and is positioned within a needle. This patent teaches using frequencies of 100 megahertz to 400 megahertz, and preferably frequencies of 500 megahertz or greater. These frequencies do not produce the necessary depth obtained with frequencies under 60 megahertz as utilized in the intra-luminal ultrasonic instrument of the present invention.

This patent teaches the rotation of a rotating member by an arrangement of small electromagnets and permanent magnets attached to a needle. The needle in this patent can only be inserted into tissue for biopsy procedures and is not adapted to be inserted into a blood vessel, nor is it intended to be inserted into a blood vessel like the catheter tip of the present invention for evaluating space around the catheter tip and particularly, the tissue or stenotic buildup located around the catheter tip to a sufficient depth.

SUMMARY OF THE INVENTION

According to the present invention, there is provided a disposable intra-luminal ultrasonic instrument for the examination and/or treatment of blood vessels and similar lumina having a small transverse cross-section, said instrument including a catheter comprising a body and a tip having a distal end and a distal portion adapted to be introduced into a lumen and a proximal portion, said catheter having a diameter no greater than 3 millimeters, a rotatable member in said tip, a small motor in said tip and coupled to said rotatable member for rotating said rotatable member at a selected rpm, and means for generating and supplying sound waves to, said rotatable member at a frequency no greater than 60 megahertz.

DESCRIPTION OF THE PREFERRED EMBODIMENT(S)

Figure 1:
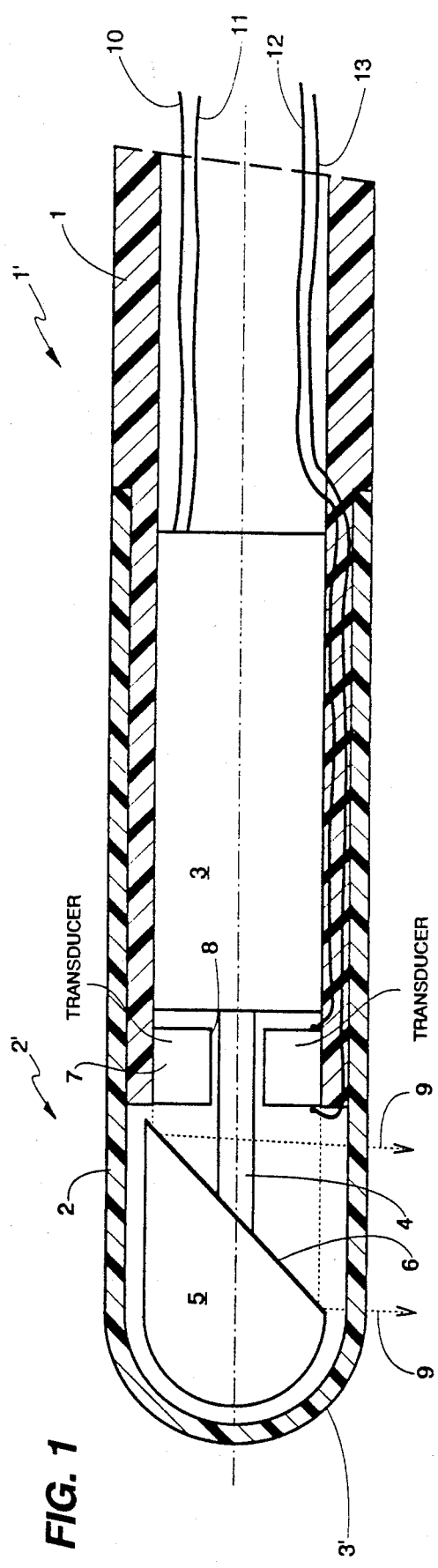
FIG. 1 is a cross-sectional view of a catheter tip of one embodiment of the disposable intra-luminal ultrasonic instrument constructed according to the teachings of the present invention.

Referring now to the Figures in greater detail, there is illustrated in FIG. 1 a catheter 1 in the form of a thin flexible tube made of a suitable disposable material, e.g., a plastic material which forms part of a disposable intraluminal ultrasonic instrument 1'. The diameter of tube 1 is not more than 2.7 millimeters and will be e.g., 0.62 millimeters, if the instrument is used for the examination and/or treatment of coronary vessels.

A small cap 2 of a suitable material, e.g. a plastic material is fastened onto a distal end portion of the flexible tube 1 to define a catheter tip 2'. The cap 2 is made of a material which is transparent to ultrasonic radiation or sound waves when the instrument is provided with means for emitting ultrasonic radiation and for receiving the echoes of the emitted radiation. In any event, the cap 2 has a window for allowing this ultrasonic radiation to pass through the cap 2.

A cylindrical motor 3 is fastened in the distal end portion of the flexible tube 1 near the distal end of the tube 1 with the motor 3 being substantially co-axial with the axis of the catheter tube 1.

In this embodiment of the instrument, 1' the motor 3 is placed at some distance from the distal end of the catheter tip 2'.

A drive shaft 4 extends distally from, is part of, and is driven by the motor 3.

A rotatable element, which in this embodiment of the instrument 1' is a rotatable acoustic mirror 5, is mounted on the drive shaft drive shaft 4 and has a mirror face 6 which lies in a plane that intersects the axis of the catheter tube 1 at an angle, as well as intersecting the axis of the drive shaft 4 of the motor 5. The mirror 5 is rotatable with and on the drive shaft 4 during operation of the motor 3.

The motor 3 can be driven at an rpm between 600 and 4,000 rpm, e.g., 1,200 rpm, 1,800 rpm, 3,600 rpm.

The rotational speed of the motor is correlated with a raster across a visual display which is connected to the instrument 1'.

A transducer 7 is mounted within the distal end portion of the catheter tube 1 between the motor 3 and the mirror face 6 opposite or facing the mirror 6.

As shown, the transducer 7 has a central passageway or channel 8 therethrough through which the drive shaft 4 extends.

Ultrasonic radiation at critically selected frequencies is emitted by the transducer 7 at the mirror face 6 and reflected outwardly by the mirror face 6 in the direction generally given by the arrows 9. This reflected bundle of radiation waves 9 emerges from the catheter tip 2' via a window formed in or defined by the cap 2.

If the ultrasound wave is reflected by an obstacle, such as an artery wall, when the catheter tip is mounted in an artery, the reflected or echoed signal so generated will pass through the window, impinge upon the mirror face 6 and will be reflected or received by the transducer 7. The reflected sound waves are then supplied by the transducer 7 to a visual display where an ultrasound image of the space surrounding the catheter tip 2' and the material in that space can be displayed on a visual display, the raster of which is coordinated with the speed of rotation of the acoustic mirror 5. The operating frequency of the sound wave will determine the depth of field of this ultrasonic imaging.

It has been found that in the megahertz frequency range lower frequencies, e.g., below 10 megahertz, will provide a deeper depth of field but with low resolution which might not be satisfactory. On the other hand, it has been found that frequencies between 45 and 60 megahertz, while providing good resolution, result in a shallower depth of field. Accordingly, in the instrument 1' of the present invention the ultrasonic sound waves generated by the transducer 7 are generated by a frequency that is not greater than 60 megahertz typically in the range of 15 and 45 megahertz, and preferably at approximately 30 megahertz.

The manner in which ultrasonic pictures can be formed of the space surrounding the catheter tip 2' with the aid of echoes or ultrasonic radiation is described in Dutch Patent application 87.00632, the disclosure of which is incorporated herein by reference.

The motor 3 is preferably a multi-polar micro-synchronized motor. The power supply for the motor 3 can be outside the catheter tube 1 with the motor 3 being coupled to the power supply by a pair of electrical wire conductors 10 and 11. These wire conductors 10 and 11 extend through the interior of the catheter tube 1 between the power supply and the motor 3 to which they are connected. The wire conductor 10 can be a current supply wire 10 and the wire conductor 11 can be a current removal, ground or common, wire 11.

Also, electrical wire conductors 12 and 13 for transmitting the electrical signals to and from the transducer 7 are received within and extend within catheter tube 1 between the transducer 7 on the distal end of the wire conductors 12 and 13 to an external drive and visual drive at the proximal drive of the wire conductors 12 and 13.

Figure 2:
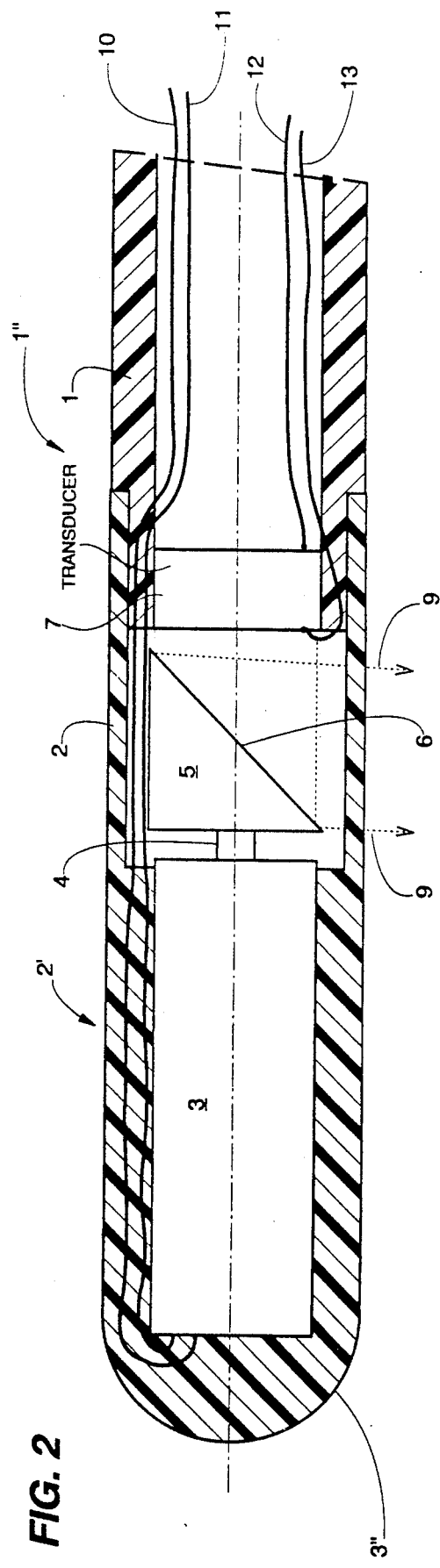
FIG. 2 is a cross-sectional view of a catheter tip, similar to the view shown in FIG. 1, of another disposable intra-luminal ultrasonic instrument constructed according to the teachings of the present invention.

In the embodiment of the disposable ultra-luminal ultrasonic instrument 1" shown in FIG. 2, the motor 3 is mounted in the outer distal end portion 3" of the cap 2. In this embodiment, the drive shaft 4 extends proximally from the motor 3 and has the mirror 5 with mirror face 6 mounted thereon. The transducer 7 is then mounted proximally of the mirror 5 opposite or facing the mirror face 6 within the flexible catheter tube 1 at the distal end thereof.

It will be appreciated that the end cap 2 and motor 3 can be constructed as an integral unit and then mounted on the distal end of the flexible catheter tube 1 with the peripheral area of the cap 2 surrounding the mirror face 6 being of reduced thickness to enable the bundle of ultrasonic waves 9 reflected by the mirror face 6 to pass through the thin wall of the cap 2 and then permit reflected sound waves or echoes to come back through the thin wall of the cap 2. The electrical wire conductors 10 and 11 for the motor 3 and the electrical wire conductors 12 and 13 for the transducer 7 again extend through the interior of the catheter tube 1, as in the embodiment of the instrument 1' shown in FIG. 1.

Figure 3:
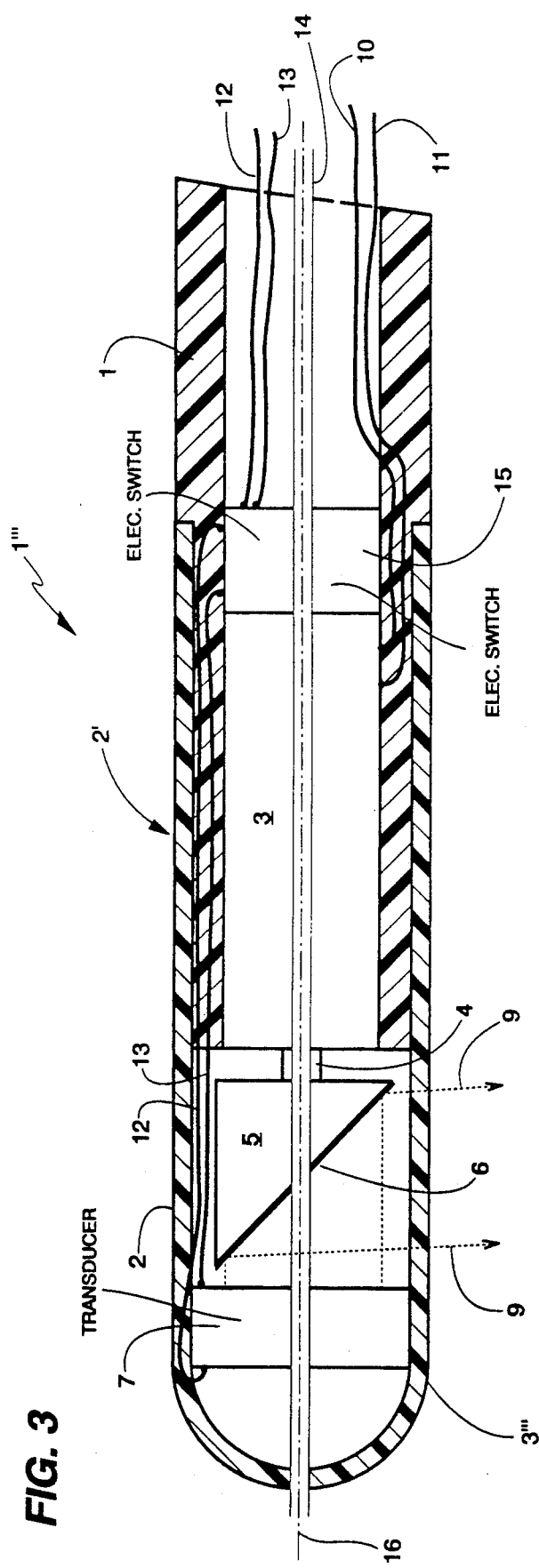
FIG. 3 is a cross-sectional view of a catheter tip, similar to the view shown in FIG. 1, of still another disposable intra-luminal ultrasonic instrument constructed according to the teachings of the present invention.

Referring now to FIG. 3, there is illustrated therein still another embodiment 1''' of the disposable intraluminal ultrasonic instrument of the present invention. This embodiment, the instrument 1''' has the transducer 7 mounted in a distal end portion 3''' of the cap 2. The motor 3 is then mounted in the distal end portion of the catheter tube 1 much the same way as the embodiment of the instrument 1' in FIG. 1. Then, the mirror 5 with a mirror face 6, similar to the mirror 5 shown in FIG. 2, is mounted between the transducer 7 and the motor 3 with the mirror face 6 facing the transducer 7 and the acoustic mirror 5 mounted on the drive shaft 4 of the motor 3.

Thus, in FIGS. 1 and 2, the mirror face 6 faces proximally of the catheter tip 2" and in FIG. 3 the mirror face 6 faces distally of the catheter tip 2'''.

Also, in the instrument 1''' shown in FIG. 3, a capillary tube 14 extends through suitable aligned bores in the motor 3, the drive shaft 4, the mirror 5, the transducer 7 and the distal end of the distal end portion 3''' of the cap 2, as well as through an electronic switch 15 mounted within the catheter tube 1 proximal of the motor 3.

With this construction of the instrument 1''', a guidewire can be inserted through the catheter tube 1, namely through the capillary tube 14 and protrude beyond the distal end of the distal end portion 3''' of the cap 2 for various known catheter procedures.

The electronic switch 15 is an integrated switch which includes circuitry for amplifying the reflected or echoed signal perceived by the transducer 7 before such signal is transmitted via the wire conductors 12 and 13 to the visual display.

Furthermore, the wire conductors 10 and 11 to the motor 3 and/or the wire conductors 12 and 13 to the transducer 7 can be used jointly as means for determining the position of a catheter in a lumen, i.e., to determine the relative position of a catheter tip 2 with respect to the surrounding space.

In the instrument 1' shown in FIG. 1, the wire conductors 12 and 13 extend from the transducer 7 through, or are embedded in, the distal end portion of the catheter tube 1 and the wire conductors 10 and 11 extend proximally from the motor 3.

In the instrument 1'' shown in FIG. 2, the wire conductors 10 and 11 are fixed in place in the distal end portion 3''' of the catheter tip 2 and extend across or intersect the path of the emitted and reflected sound waves 9 and then through the distal end portion of the catheter tip portion 1 to the interior of the catheter tube 1. Thus, the portion of the wire conductors 10 and 11 in the vicinity of the mirror 5 will be seen on the visual display so that the position of the catheter tip relative to the area of the lumen or blood vessel under investigation can be determined.

Likewise, the position of a portion of the wires 12 and 13 extending within the cap 2 in the vicinity of the mirror 5 can be seen on the visual display for determining the orientation and location of the catheter tip 2'' relative to the area of the lumen or blood vessel under investigation.

This orientation method is comparable to the orientation method described in Dutch Patent Application No. 89.01084, the disclosure of which is incorporated herein by reference.

From the foregoing description of the embodiments 1', 1'', 1''' shown in FIGS. 1-3, the positions, respectively, of the motor 3, the mirror 5 and the transducer 7 can be adjusted as desired.

The mirror face 6 is angled to the catheter axis in a manner as taught in Dutch Patent Application No. 87.00632.

In the embodiment shown in FIG. 1, the transducer 7 has a central channel 8 through which the drive shaft 4 can extend.

The motor 3 of the intra-luminal ultrasonic instrument 1', 1'' or 1''' is substantially cylindrical in an appropriate shape and has a length of less than approximately 6 millimeters, and preferably approximately less than 4 millimeters, and a diameter of not more than approximately 2.4 millimeters, preferably not more than approximately 1 millimeters.

Also, as described above, devices such as the electrical wire conductors in their position can be utilized for determined the orientation of the catheter tip with respect to the surrounding space as taught in Dutch Patent Application No. 89.01084.

The instrument 1', 1'' or 1''' can be fitted in a suitable manner with devices to perform an examination inside the artery or vein after the examination has taken place, or even during the examination, to use an obstructive method, for example, for destroying plaque.

The instrument 1', 1'' or 1''' can, for example, be fitted with devices to perform the spark erosion method, as described in the Dutch Patent Application No. 87.00632.

It is also possible to provide the instrument 1', 1'' or 1''' with a balloon for use in a balloon dilation method which is well known in the field of angioplasty. In the practice of an angioplasty method, a suitable balloon can be fastened around the catheter tip 2'' and a separate channel can be built in along the catheter tube 1 which is connected to the balloon for inflating it while operating it and thereafter allowing the balloon to deflate.

As described in connection with the description of FIG. 3, a central channel or capillary tube 14 can be provided for receiving a guidewire 16 through the catheter tube 1 and the catheter tip 2''.

The space in the catheter tip 2'' where the transducer 7 and mirror tip 5 are located is primarily filled with a liquid before operating the instrument 1', 1'' or 1''' to ensure efficient acoustical operation of the instrument 1', 1'' or 1'''. The above referred to space can be pre-evacuated using vacuum techniques and liquid can be sucked into the space via suitable channels. It is also possible to directly introduce liquid into the space via a filling tube so that the air or other gas present is expelled via suitable degassing channels in the catheter tube 1. The filling tube can be a separate lumen in the catheter tube 1 or can be a small tube fitted along or in the catheter tube 1 itself and which can be pulled away after use.

Furthermore, an integrated switch 15, as shown in FIG. 3, can be mounted in the catheter tip 2'' of the instrument 1', 1'', or 1''' adjacent the motor 3 and the transducer 7. This structural arrangement assists in the amplification of the echo signal emitted by the transducer 7 before it is transmitted by the wire conductors 12 and 13 to the visual display; and such amplification allows certain, otherwise necessary, structure in or on the catheter tip 2' to be emitted, e.g., the provision of a metal wire wound spirally around the catheter mantle, and working as a Faraday's cage, and concealed within the catheter tip 2' and the catheter tube 1 can be omitted.

The instrument 1', 1'' or 1''' works well with a French 5 catheter having a diameter of approximately 1.6 millimeters.

Furthermore, the transducer 7 is constructed, arranged and operated to emit sound waves at no more than 60 megahertz, typically somewhere between 15 and 45 megahertz, and at one preferred use of the instrument 1' 1'' or 1''' at approximately 30 megahertz.

It has been found that the frequencies used, particularly approximately 30 megahertz, results in an ultrasound picture having a depth of field of at least one-half inch ($\frac{1}{2}$'') with good resolution so that the makeup or constitution, e.g., hard calcified or soft fatty material, of the tissue or stenotic buildup being investigated can be determined. Furthermore, the instrument 1', 1'' or 1''' having the constructions described above with reference to FIGS. 1-3, are constructed in a simple and inexpensive manner which allows the instrument 1', 1'' or 1''' to be a disposable instrument.

From the foregoing description, it will be apparent that the instrument 1', 1'' or 1''' of the present invention have a number of advantages, some of which have been described above and others which are inherent in the invention. Accordingly, the scope of the invention should only be limited as necessitated by the accompanying claims.

We claim:

1. A disposable intra-luminal catheter probe type ultrasonic instrument for the examination and/or treatment of blood vessels having a small transverse cross-section, said instrument including a flexible, guidewire receiving, catheter comprising a body and a tip having a distal end and a distal end portion adapted to be introduced into a lumen of a blood vessel and a proximal portion, said catheter having a diameter no greater than 3 millimeters, and a small motor in said tip having a length no greater than approximately 6 millimeters, a diameter no greater than approximately 2.4 millimeters and drive shaft extending from one end of said motor, a rotatable member having an acoustical mirror face mounted in said tip and one said drive shaft for being rotated by said motor at a selected rpm synchronized with a raster across a visual display to which echoes of sound waves received by said mirror face are supplied, the angular position of the acoustic mirror face being oriented to correspond to the angle of an echo display line on the visual display, and means including a transducer facing said mirror face for generating and supplying sound waves along an axis of propagation to said rotatable acoustical mirror face at a frequency no greater than 60 megahertz for reflection therefrom to obtain a sufficient depth of field with sufficient resolution to determine the makeup or constitution of the matter, such as tissue or plaque, in the space being investigated around said catheter tip, said rotatable acoustic mirror face being located in said distal end portion, and said mirror face lying in a plane that intersects, at an angle, the axis of the drive shaft and the axis of the propagation of sound waves from said means for generating sound waves.

2. The instrument of claim 1 wherein said motor has a side which faces toward said distal end and said drive shaft extends from said side facing said distal end.

3. The instrument of claim 2 wherein said transducer is mounted in said tip between said rotatable member and said motor and has a central passageway therethrough through which said drive shaft extends.

4. The instrument of claim 1 wherein said drive shaft extends proximally from said distal end of said catheter tip, and said transducer is positioned in said tip opposite said mirror face, which faces proximally from said distal end of said catheter tip.

5. The instrument of claim 2 wherein said transducer is mounted within said distal end portion at said distal end of said catheter tip and faces proximally toward said mirror face which faces distally.

6. The instrument of claim 1 wherein said motor has a length no greater than approximately 4 millimeters and a diameter no greater than approximately 1 millimeter.

7. The instrument of claim 1 wherein said catheter includes electrical conductors for supplying electric power to said motor and to said sound wave generating means.

8. The instrument of claim 1 wherein said catheter has a central channel that also extends through said sound wave generating means and through said shaft through and to said distal end of said tip distal end portion, and said instrument includes a flexible guidewire which is extendable through said central channel.

9. The instrument of claim 1 wherein said sound waves are generated at a frequency of between approximately 15 and 45 megahertz.

10. The instrument of claim 1 wherein said means for generating sound waves are constructed and arranged to generate sound waves at a frequency of approximately 30 megahertz.

11. A disposable intra-luminal catheter probe type ultrasonic instrument for the examination and/or treatment of blood vessels lumina having a small transverse cross-section, said instrument including a flexible, guidewire receiving, catheter comprising a body and a tip having a distal end and a distal end portion adapted to be introduced into a lumen of a blood vessel and a proximal portion, said catheter having a diameter no greater than 3 millimeters, a rotatable member having an acoustical mirror face mounted in said tip, a small motor mounted in said tip and having a drive shaft mounting said rotatable member for rotating said rotatable member at a selected rpm, and mean including a transducer facing said mirror face for generating and supplying sound waves to said rotatable member along an axis of propagation at a frequency no greater than 60 megahertz for reflection by said mirror face to obtain a sufficient depth of field with sufficient resolution to determine the makeup or constitution of the matter, such as tissue or plaque, in the space being investigated around said catheter tip, said mirror face lying in a plane that intersects, at an angle, the axis of the drive shaft and the axis of propagation of sound waves from said means for generating sound waves, said motor having a side which faces toward said distal end, said drive shaft extending from said side facing said distal end, and said transducer being mounted in said tip between said rotatable member and said motor and having a central passageway therethrough through which said drive shaft extends.

* * * * *